United States Patent [19]

Genese et al.

[11] 4,252,116

[45] Feb. 24, 1981

[54] EQUIPMENT SETS HAVING A NOVEL FLEXIBLE DIAPHRAGM VALVE IN A SECONDARY LIQUID FLOW PATH FOR THE SEQUENTIAL ADMINISTRATION OF MEDICAL LIQUIDS AT DUAL FLOW RATES

[75] Inventors: Joseph N. Genese, Waukegan; Andrew J. Muetterties, Gages Lake, both of Ill.

[73] Assignee: Abbott Laboratories, North Chicago, Ill.

[21] Appl. No.: 16,269

[22] Filed: Feb. 28, 1979

[51] Int. Cl.³ .............................................. A61M 5/14
[52] U.S. Cl. ............................... 128/214 G; 128/274; 137/113; 137/859; 222/145
[58] Field of Search ........... 128/214 R, 214 L, 214 G, 128/214.2, 227, 274; 222/129.2, 145; 137/112–114, 859

[56] References Cited

U.S. PATENT DOCUMENTS

| 926,197 | 6/1909 | Kim | 128/227 |
|---|---|---|---|
| 3,633,605 | 1/1972 | Smith | 137/113 |
| 3,886,937 | 6/1975 | Bobo et al. | 128/214 G |
| 4,105,029 | 8/1978 | Virag | 128/214 G |
| 4,116,646 | 9/1978 | Edwards | 128/214 R X |

FOREIGN PATENT DOCUMENTS

| 1099294 | 2/1961 | Fed. Rep. of Germany | 137/113 |
|---|---|---|---|
| 1375258 | 9/1964 | France | 137/859 |

*Primary Examiner*—Dalton L. Truluck
*Attorney, Agent, or Firm*—Robert L. Niblack; Aaron L. Hardt; Robert S. Beiser

[57] ABSTRACT

Equipment sets for the sequential administration of medical liquids wherein a primary liquid can be administered at a flow rate independent of the flow rate of a secondary liquid, and including a barrier substantially impervious to air to prevent the inadvertent administration of air when the secondary liquid is depleted. The sets of this invention employ a novel flexible diaphragm valve as the air barrier.

21 Claims, 5 Drawing Figures

EQUIPMENT SETS HAVING A NOVEL FLEXIBLE DIAPHRAGM VALVE IN A SECONDARY LIQUID FLOW PATH FOR THE SEQUENTIAL ADMINISTRATION OF MEDICAL LIQUIDS AT DUAL FLOW RATES

BACKGROUND OF THE INVENTION

The present invention relates to systems and equipment sets for the administration of medical liquids to a patient, and more particularly, to systems and equipment sets for the sequential administration of a plurality of medical liquids employing a novel flexible diaphragm valve in the flow path of one liquid to prevent the passage of air through that path when the liquid becomes depleted.

The parenteral administration of medical liquids to patients is a long established practice. Liquids including amino acids, blood, dextrose, electrolytes, and saline are commonly administered to patients over prolonged periods of time. Generally, these liquids are administered from a glass bottle or plastic bag suspended above the patient and containing 250-2,000 ml. of the liquid. Such prolonged infusions commonly are administered at a flow rate of 10-150 ml./hr.

Frequently, the patient must receive an additive or secondary liquid while the prolonged infusion is being administered. Preferably, this secondary liquid should be administered through the same hypodermic needle to avoid unnecessary pain and trauma to the patient of additional venipunctures. To avoid dilution and incompatability problems, it is also preferable that the flow of the primary liquid employed in the prolonged infusion be temporarily interrupted, the secondary liquid administered and the flow of the primary liquid resumed. Generally, the secondary liquid will be administered at a flow rate of 50-250 ml./hr.

Abbott Laboratories, North Chicago, Illinois manufactures a y-type set for the sequential administration of primary and secondary liquids. These VENOSET piggyback sets allow the prolonged infusion of a primary liquid to be temporarily halted by means of a backcheck valve in the primary liquid flow path to administer a secondary liquid without the need for a new venipuncture. Then, when the secondary liquid has been depleted, the backcheck valve automatically opens to resume flow of the primary liquid. An important characteristic of this system is that the secondary liquid container must be suspended at a higher height than the primary liquid container to establish the liquid pressure differential that closes the backcheck valve in the primary liquid flow path.

A similar system is disclosed in U.S. Pat. No. 3,886,937 granted June 3, 1975 to D. Bobo, et al., assigned to American Hospital Supply Corp., and entitled "Medical Administration Set for Dispensing Plural Medical Liquids". Another similar system is disclosed in U.S. Pat. No. 4,105,029 granted Aug. 8, 1978 to R. Virag, assigned to Baxter Travenol and entitled "Intravenous Solution Set Having An Air Access Site and Constricted Inner Diameter Portion".

An inherent disadvantage of the above-mentioned prior art medical liquid administration systems is that they each resume the flow of primary liquid at the rate the secondary liquid had been flowing. Because the preferred flow rate of the secondary liquid is generally greater than the preferred flow rate of the primary liquid, when the primary liquid resumes flow at that rate, the patient can be administered an excessive amount of primary liquid, unless the flow rate of the primary liquid is adjusted to the preferred primary liquid flow rate soon after the flow of primary liquid resumes.

A remedy to the above-described disadvantage would appear to be provided by simply incorporating flow control devices into both the primary and secondary liquid flow paths. However, while this remedy does provide dual flow rates for the primary and secondary liquids, it is unacceptable. That is, because the common tube of the y-set must be able to accommodate both flow rates, when the primary liquid is flowing at a slower rate than the secondary liquid was, there will be an unfilled volume or void in the common tube. To fill that void, air will be drawn into the common tube from the depleted secondary container. That air will then be driven into the patient by the weight of the primary liquid, thereby causing a serious embolism and perhaps, the patient's death.

Accordingly, it will be apparent that an efficacious system for the sequential administration of medical liquids at dual flow rates would be advantageous to the medical profession.

SUMMARY OF THE INVENTION

The primary object of the present invention, therefore, is to provide an equipment set for the sequential administration of medical liquids at dual flow rates that will not draw air from the secondary container when the secondary liquid has been depleted.

In accordance with this and other objects, there is provided by the present invention an equipment set for the sequential administration of medical liquids to a patient including a primary tube, a secondary tube, and a common tube all connected in fluid communication to form a primary liquid flow path and a secondary liquid flow path. The primary liquid flow path includes the primary and common tube, while the secondary liquid flow path includes the secondary and common tubes.

The primary tube includes a primary valve which allows primary liquid to flow from a primary liquid container whenever the height of primary liquid is greater than or equal to the height of the secondary liquid in the system. The primary valve, which can be a backcheck valve, prevents primary liquid from flowing out of the primary container whenever the height of the primary liquid is less than the height of the secondary liquid in the system.

To establish the dual flow rates of the primary and secondary liquids, a secondary flow control means in the secondary liquid flow path for adjusting the flow rate of the secondary liquid and a primary flow control means on the primary tube for adjusting the flow rate of the primary liquid to a rate greater than, less than, or equal to the flow rate of the secondary liquid are provided. A novel flexible diaphragm valve is provided as an air barrier in the secondary liquid flow path. The diaphragm is substantially impervious to air and liquid to insure that no air is drawn from the secondary container when the secondary liquid is depleted.

BRIEF DESCRIPTION OF THE DRAWING

Other objects and attendant advantages will become obvious to those skilled in the art by reading the following detailed description in connection with the accompanying drawing, wherein like reference characters designate like or corresponding parts throughout the several figures thereof and wherein.

DETAILED DESCRIPTION OF THE INVENTION

Figure 1:
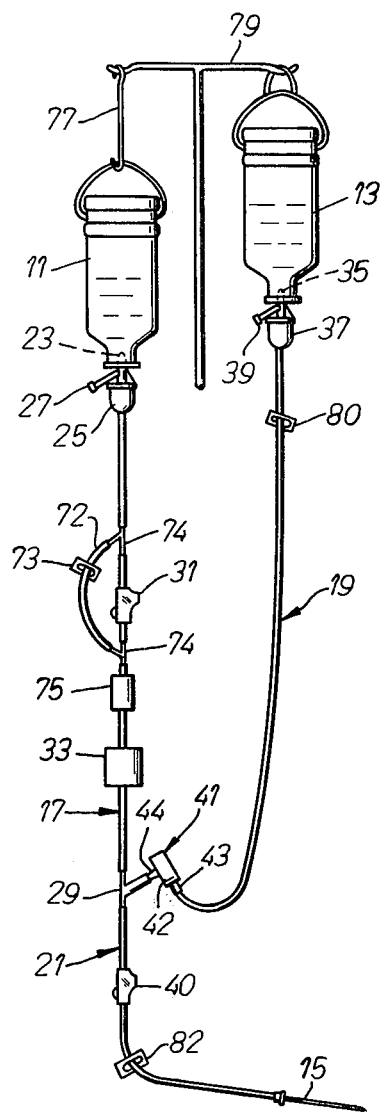
FIG. 1 is a front elevational view of one embodiment of the efficacious equipment sets for the sequential administration of medical liquids at dual flow rates contemplated by this invention.
Figure 3:
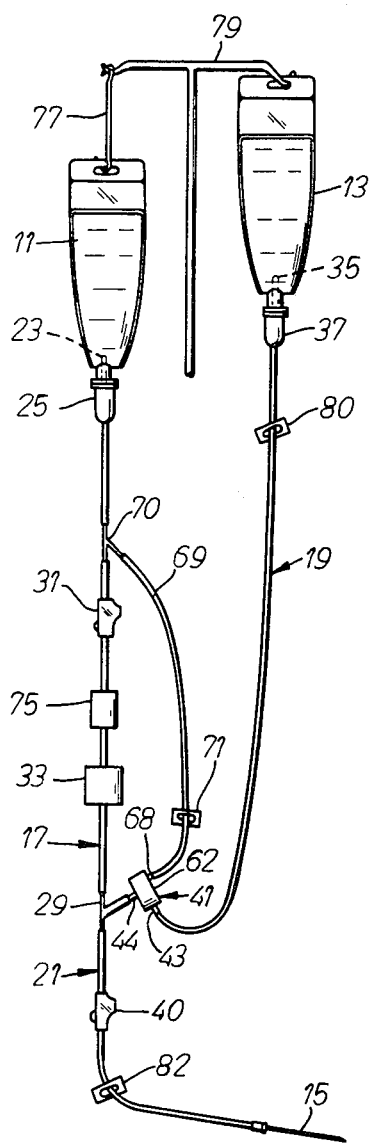
FIG. 3 is a front elevational view of another embodiment of the efficacious equipment sets for the sequential administration of medical liquids at dual flow rates contemplated by this invention.

Referring to the drawing, there is shown in FIGS. 1 and 3, two embodiments of the basic elements of the equipment sets for the sequential administration of medical liquids at dual flow rates contemplated by this invention.

FIGS. 1 and 3 depict a primary liquid container 11 that contains a primary medical liquid to be administered to a patient for a prolonged period of time. FIGS. 1 and 3 also depict a secondary liquid container 13 that contains a secondary medical liquid to be administered to the patient for a relatively short period of time, during which time the administration of the primary liquid will be temporarily interrupted. As shown in the sets of FIGS. 1 and 3, containers 11 and 13 can be glass bottles, plastic flexible bags, or any other suitable container.

Primary container 11 and secondary container 13 are connected in fluid communication to a conventional hypodermic needle 15 through a primary tube 17, a secondary tube 19, and a common tube 21. Thus, the primary liquid flow path from primary container 11 to needle 15 comprises primary tube 17 and common tube 21. Likewise, the secondary liquid flow path from secondary container 13 to needle 15 comprises secondary tube 19 and common tube 21.

The distal end of primary tube 17 is in fluid communication with primary container 11, preferably by means of a piercing pin 23 inserted into a puncturable closure of container 11. Piercing pin 23 can have an integral drip chamber 25, and when container 11 is a glass bottle, as shown in the set of FIG. 1, an integral, filtered air vent 27. Such piercing pins, drip chambers and air vents are well known in the medical practice and need not be more fully explained here.

The proximal end of primary tube 17 is joined in fluid communication to the distal end of common tube 21, preferably by a y-tube 29, it being understood that the primary, secondary and common legs of y-tube 29 constitute a portion of the primary, secondary and common tubes 17, 19 and 21, respectively. Primary tube 17 has a primary flow control 31 intermediate its ends for independently adjusting the rate of flow of the primary liquid through the primary liquid flow path. Preferably, as shown in FIGS. 1 and 3, primary flow control 31 can be a roller clamp. However, it can be any other adjustable device that will reliably maintain a desired primary liquid flow rate.

Primary tube 17 includes a primary valve 33 between its proximal end and primary flow control 31. Primary valve 33 allows primary liquid to flow from primary container 11 whenever the height of the primary liquid is greater than or equal to the height of the secondary liquid in the system. Further, primary valve 33 prevents the flow of primary liquid from primary container 11 whenever the height of the primary liquid is less than the height of the secondary liquid in the system.

While primary valve 33 has been shown in the sets of FIGS. 1 and 3 as being spaced from the proximal end of primary tube 17, it will be readily apparent that primary valve 33 can be incorporated into the primary leg of y-tube 29, if so desired. For example, primary valve 33 can be a conventional, one-way, backcheck valve mounted within the primary leg of y-tube 29.

The distal end of secondary tube 19 is in fluid communication with secondary container 13, preferably, by means of a piercing pin 35 inserted into a puncturable closure of container 13. Piercing pin 35 can have an integral drip chamber 37, and when container 13 is a glass bottle, as shown in FIG. 1, an integral, filtered air vent 39. The proximal end of secondary tube 19 is joined in fluid communication to the distal end of common tube 21, preferably, by a y-tube 29.

An air barrier 41 and secondary flow control 40 are located in the secondary liquid flow path. Preferably, as shown in FIGS. 1 and 3, secondary flow control 40 can be a roller clamp. However, it can be any other adjustable device that can reliably maintain a desired secondary liquid flow rate.

As shown in FIGS. 1 and 3, an air barrier 41 is located in secondary tube 19. While air barrier 41 is shown near the proximal end of secondary tube 19, it will be readily apparent that air barrier 41 can be more distally located on secondary tube 19, or incorporated into the secondary tube leg of y-tube 29, if so desired.

Figure 2:
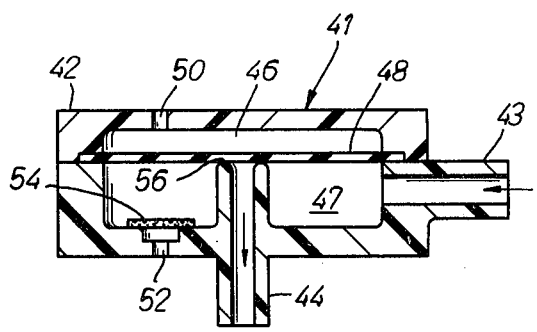
FIG. 2 is a front elevational view in cross-section of the flexible diaphragm valve depicted in FIG. 1.

As shown in the set of FIG. 1, air barrier 41 comprises a valve housing 42 having an inlet 43 and outlet 44 in fluid communication with secondary tube 19 and constitutes a portion of it. As best seen in FIG. 2, housing 42 is divided into two chambers 46, 47 by an air and liquid impermeable, flexible diaphragm 48. Diaphragm 48 is, preferably, made of elastomeric material, such as natural or silicone rubber. Diaphragm 48 can also be made of thermoplastic materials, such as polyethylene. As shown in FIG. 2, diaphragm 48 can be captured between halves of housing 42. Alternatively, diaphragm 48 can be insert-molded into a single piece housing.

Chamber 46 has an an air vent 50 through housing 42 by which ambient air can enter and exit. Chamber 47 has an air vent 52 through which ambient air can enter and exit. Air vent 52 is covered by a hydrophobic membrane 54 which is permeable by air, but not liquids. The hydrophobic filters can be formed of polyfluorotetraethylene, hexafluoropropylene/tetrafluoroethylene copolymer, or other suitable materials. One such filter is made of Gelman ANH-450 material made by Gelman Instruments of Ann Arbor Michigan.

As seen in FIG. 2, outlet 44, preferably, extends into chamber 47 a substantial distance and its inner end 56 forms a seat on which flexible diaphragm 48 is normally seated to close outlet 44 to air and liquid.

Figure 4:
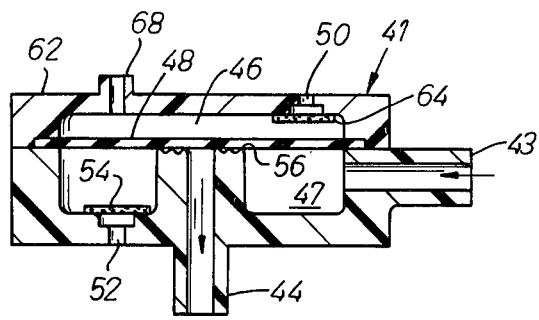
FIG. 4 is a front elevational view in cross-section of the flexible diaphragm valve depicted in FIG. 3.
Figure 5:
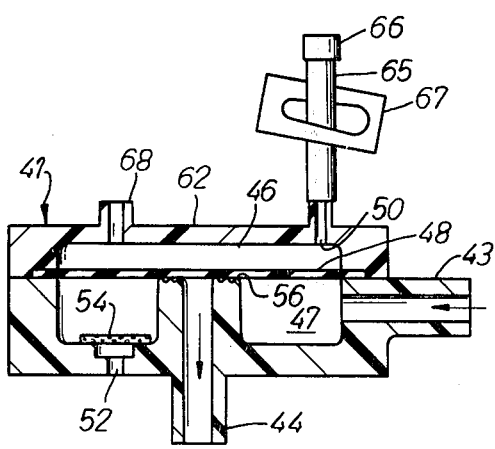
FIG. 5 is a front elevational view in cross-section of an alternate embodiment of the flexible diaphragm valve of FIG. 4.

As shown in the set of FIG. 3, air barrier 41 comprises a valve housing 62 having an inlet 43 and outlet 44 in fluid communication with secondary tube 19 and constitutes a portion of it. As best seen in FIGS. 4 and 5, housing 62 is divided into two chambers 46, 47 by an air and liquid impermeable membrane 48. Chamber 46 has an air vent 50 covered by a hydrophobic membrane 64. Alternatively, as shown in FIG. 5, air vent 50 can include a tube 65 having a filtered end 66 and a slide clamp 67 which can be slide to open vent 50 to the passage of air and closed to prevent the passage of liquid.

Housing 62 has a port 68 therethrough and opening into chamber 46. As seen in FIG. 3, port 68 is connected in fluid communication to primary tube 17 by a pilot tube 69, preferably, by means of a y-tube 70. Pilot tube 69 has a slide clamp 71 thereon for controlling the flow of liquid through pilot tube 69. When slide clamp 71 is open, primary liquid can enter housing 62 to further bias flexible membrane 48 to its normally closed position. The entering primary liquid forces air from chamber 46 through vent 50. However, the primary liquid is prevented from flowing through vent 50 by hydrophobic membrane 64. When the alternative embodiment of FIG. 5 is used, slide clamp 65 must also be open to enable liquid to enter chamber 46 and slide clamp 71 can be eliminated, if so desired.

As shown in FIGS. 4 and 5, chamber 47 of housing 62 has an air vent 52 covered by a hydrophobic membrane 54. Alternatively, vent 52 can include a tube having a filtered end and slide clamp similar to that of vent 50, if so desired. The inner end 56 of outlet 44 from chamber 47 is provided a plurality of protrusions to form a plurality of seats on which flexible diaphragm 48 can seat. Preferably, the plurality of protrusions are formed by a plurality of concentric rings of unequal heights, the height of the respective rings decreasing in a direction from the perimeter of inner end 56 towards its center.

In the set of FIG. 1, primary tube 17 includes a priming tube 72 having a slide clamp 73 that controls the flow of primary liquid through priming tube 72. Priming tube 72 is joined in parallel to the main branch of primary tube 17 by y-tubes 74, located on each side of primary control means 31. As will be more fully explained in the following paragraphs, priming tube 17 allows primary control means 31 to remain at its preferred adjustment while the set of FIG. 1 is being primed or back-primed at a higher flow rate.

Primary flow control 31 is shown on the distal side of primary valve 33 in FIGS. 1 and 3. It has been found that for pressure differentials of the magnitude occuring in the system of this invention, location of primary flow control 31 on the proximal side of primary valve 33, for most of the preferred settings of primary flow control 31, results in a greater pressure being exerted on primary valve 33 by primary liquid than by secondary liquid. As a result, primary valve 33 remains open, as if the height of primary liquid were greater than or equal to the height of secondary liquid in the system.

Surprisingly, it has been found that when primary flow control 31 is located on the distal side of primary valve 33, as shown in FIGS. 1 and 3, certain embodiments of primary valve 33 might not remain closed as expected whenever the height of primary liquid is less than the height of secondary liquid in the system. This unexpected opening results from the reaction force on primary valve 33 caused by primary liquid that cannot flow upwardly past primary flow control 31 when primary valve 33 initially closes. This reaction force reopens valve 33 and keeps it open.

It has been found that this unexpected opening of primary valve 33 can be obviated by the inclusion in primary tube 17 of a chamber 75 for a compressible mass. As shown in FIGS. 1 and 3, chamber 75 is located between primary flow control 31 and primary valve 33 and provides a cushion or spring for relieving pressures on the distal side of primary valve 33 whenever valve 33 closes in response to the height of primary liquid being less than the height of secondary liquid in the system. Although primary valve 33 and chamber 75 are shown as separate units in FIGS. 1 and 3, it will be apparent that they can be combined into one unit, if so desired.

As shown in the sets of FIGS. 1 and 3, chamber 75 has a housing with an inlet and outlet in fluid communication with primary tube 17. However, it is contemplated that chamber 75 can have only one opening in communication with primary tube 17. That is, chamber 75 may have a single opening transverse to the normal flow of liquid through primary tube 17 so that primary liquid only flows in or out of its single opening when reverse flow pressures exist on the distal side of primary valve 33.

Generally, the compressible mass of chamber 75 will be air and its housing will be a rigid opaque plastic. However, it is contemplated that the compressible mass of chamber 75 can be a sponge or other flexible solid materials, as well. Further, the housing of chamber 75 can be a flexible material which is compressible by the primary liquid to expand chamber 75, if so desired.

The sets shown in FIGS. 1 and 3 each include a slide clamp 80 near the distal end of secondary tube 19 and a slide clamp 82 near the proximal end of common tube 21.

For simplicity, the equipment sets of FIGS. 1 and 3 have been depicted and described as integral units. It is apparent, however, that the sets can be manufactured and assembled in subsets of the entire set and that each subset will accordingly be provided such resealable closures, piercing means, adapters etc. as are necessary to permit their easy assemblage into the complete set at an appropriate time. It will also be apparent that each of the several components of the sets of FIGS. 1 and 3 can be interchanged or combined in combinations other than those specifically depicted.

Operation of the System

As depicted in FIGS. 1 and 3, primary container 11 is suspended in space at a height above the patient by means of a hook 77 and stand 79. It will be apparent that other means for suspending the containers of this invention are well known.

To insure that all the air that might be forced into the patient has been removed from the set, the set is initially primed by first closing all slide clamps 67, 71, 73, 80 and 82, if present. Piercing pin 23 is then inserted into the puncturable closure of primary container 11. Primary flow control 31 and secondary flow control 40 are fully opened. Slide clamp 82 is opened to allow primary liquid to flow through the primary liquid flow path and force all the air therefrom that might be forced into the patient. If chamber 75 is present in primary tube 17, a substantial volume of air will remain therein. Slide clamp 82 is then closed.

If inlet 43 to air barrier 41 is closed by a resealable closure at this time, secondary tube 19 will have been backprimed while primary tube 17 was being primed. When secondary tube 19 is backprimed, chamber 47 will be flooded so that all of diaphragm 48 will be contacted by primary liquid that will hydrostatically lift diaphragm 48 from outlet 44 to fully open the valve. As primary liquid enters chamber 47, diaphragm 48 will flex away from outlet 44 and air will be expelled through air vent 52 in chamber 47 and air vent 50 in chamber 46. However, hydrophobic membrane 54 will prevent the flow of liquid through vent 52.

Alternatively, if the set is fully assembled, slide clamp 80 can be opened to allow primary liquid to force air out of the entire secondary tube 19. Slide clamp 80 is then closed. During this initial priming of secondary tube 19, it is advantageous to hold secondary tube 19 at a height well below primary container 11. When secondary tube 19 has been primed, it is secured in a convenient place until its subsequent use.

Common tube 21, which preferably has an adapter at its proximal end open to the flow of liquid therefrom, is next connected to needle 15, which will generally have been already inserted into a vein of the patient. Slide clamp 82 will then be opened to allow primary liquid to flow through the primary liquid flow path to the patient's vein. Primary flow control 31 is then adjusted to a setting that will provide the desired flow rate for a prolonged infusion of primary liquid into the patient, generally 10–150 ml./hr. As is well known in the medical practice, that flow rate can be visually observed by viewing and counting drops passing through the primary drip chamber 25.

Subsequently, when it is desired to administer a secondary liquid to a patient, piercing pin 35 of secondary tube 19 is inserted into the puncturable closure of secondary container 13. If any portion of secondary tube 19 has not already been primed, it can now be primed with secondary container 13 held at a height well below primary container 11, secondary tube slide clamp 80 opened, common tube slide clamp 82 closed and priming tube slide clamp 73, if present, opened.

Primary liquid then is allowed to flow into, or backprime, secondary tube 19 until all the air that can be forced into the patient has been expelled from secondary tube 19. If present, priming tube 73 allows the primary liquid to bybass the primary flow control and flow into secondary tube 19 at the fastest possible rate.

Secondary container 13 is then suspended in space from stand 79 at a height substantially greater than the height of primary container 11, thereby immediately causing primary valve 33 to close. Priming tube slide clamp 73, if present, is then closed and common tube slide clamp 82 opened.

If the sets of FIG. 3 are being used, slide clamps 67 and/or 71 are opened to allow primary liquid to enter chamber 46 of valve housing 62 at this time. If this pilot liquid enters chamber 46 before secondary tube 19 is fully backprimed, it will not be possible to back-prime secondary tube 19 as the weight of the liquid will prevent membrane 48 from lifting away from outlet 44. It will be apparent that none of the pilot liquid entering chamber 46 through pilot tube 69 will be administered to the patient.

Secondary flow control 43 is then adjacent to a desired flow rate, typically 50–250 ml./hr., for the secondary liquid, which will then flow until the secondary container 13 is depleted. It will be apparent that the initial liquid flowing from secondary tube 19 will be the primary liquid with which it was primed.

When the height of primary liquid in the sets of FIGS. 1 and 3 becomes greater than the height of the secondary liquid, primary valve 33 will immediately open and allow primary liquid to flow from the primary container at the flow rate to which primary flow control 31 is adjusted. The primary flow rate is independent of the secondary flow rate. In those instances where it is less than or equal to the secondary flow rate, both primary and secondary liquid will flow through common tube 21, until air reaches air barrier 41 in the secondary tube. The only primary liquid will enter common tube 21. Air barrier 41 then prevents air from being drawn into common tube 21 and eventually to the patient's vein.

Diaphragm 48 of valve housing 42 shown in FIG. 1 will now seat against outlet 44 because of its own weight and elastic memory. Air will re-enter chamber 46 through air vent 50 as diaphragm 48 seats. Secondary liquid will remain in chamber 47 at a level just below diaphragm 48. As primary liquid flows through common tube 21 on the proximal side of diaphragm 48, it will create a reduced pressure that will tend to draw diaphragm 48 into outlet 44 even further. In addition, diaphragm 48 of housing 62 will be further biased against outlet 44 by the weight of the primary liquid present in chamber 46, when that valve is employed.

When primary container 11 becomes depleted of primary liquid, the primary piercing pin 23 is merely removed therefrom and inserted into the resealable closure of a new primary container, which is then suspended in place of the previous container. If primary container 11 had become empty, it will be necessary to reprime the entire system as when the first primary container was administered.

When secondary container 13 becomes depleted of secondary liquid, it can be left empty until another secondary liquid is to be administered. When another secondary liquid is to be administered, the secondary piercing pin 35 is merely removed from secondary container 13 and inserted into a new secondary liquid container. The pilot liquid must be drained from chamber 46, if present. The secondary tube 19 must then be backprimed, as when the first secondary container was administered.

Having described the invention in specific detail and exemplified the manner in which it may be carried into practice, it will now be readily apparent to those skilled in the art that innumerable variations, applications, modifications and extensions of the basic principles involved may be made without departing from its sphere or scope.

I claim:

1. In a set for the sequential administration of medical liquids to a patient, said set including:
   a primary tube for the flow of a primary medical liquid therethrough and including a primary valve for controlling the flow of liquid through said primary tube,
   a secondary tube for the flow of a secondary medical liquid therethrough,
   said primary valve permitting the flow of primary liquid therethrough and preventing the flow of secondary liquid into said primary tube,
   a common tube having its distal end in fluid communication with the proximal ends of said primary and secondary tube and its proximal end open for the flow of liquid therefrom to form a primary liquid flow path comprising said primary tube and said common tube and a secondary liquid flow path comprising said secondary tube and said common tube, the improvement which comprises:
   a secondary flow control means in said secondary liquid flow path for adjusting the flow rate of said secondary liquid therethrough, a primary flow control means on said primary tube for adjusting the flow rate of said primary liquid through said primary flow path to a rate independent of the flow rate of said secondary liquid through said secondary liquid flow path, and an air barrier in said secondary liquid flow path substantially impervious to air for preventing the flow of air therethrough and for permitting the passage of said secondary liquid therethrough, wherein said air barrier is a mechanical valve comprising a housing divided into first and second chambers by an air and liquid impermeable, flexible diaphragm normally biased against and sealing an outlet from said second chamber, said first chamber having an air vent through said housing and said second chamber having an air vent through said housing with means associated therewith to prevent the flow of liquid therethrough, an inlet connected in fluid communication with said secondary tube for the entrance of secondary liquid into said second chamber, said outlet from said second chamber being connected in fluid communication to said common tube for the exit of said secondary liquid from said second chamber, when present but said outlet normally being closed to air and liquid by said diaphragm.

2. The set defined in claim 1, wherein said set is further characterized by a port to said first chamber through said housing connected in fluid communication to the proximal end of a primary liquid pilot tube which is connected in fluid communication at its distal end to said primary tube distally to said primary flow control means for the flow of primary liquid into and out of said first chamber, and said air vent of said first chamber has means associated therewith to prevent the flow of liquid therethrough, whereby said primary liquid entering said first chamber serves to bias said flexible diaphragm against said outlet.

3. The set defined in claim 1 or 2, wherein said outlet is further characterized in that its inner end extends into said second chamber to form a seat on which a portion of said diaphragm seats to normally close said outlet.

4. The set defined in claim 3, wherein said inner end had a plurality of protrusions to form a plurality of said seats.

5. The set defined in claim 4, wherein said plurality of protrusions are concentric rings of unequal heights, the height of said rings decreasing in a direction from the perimeter of said inner end towards the center thereof.

6. The set defined in claim 1 or 2, wherein said means associated with said air vent of said second chamber is a hydrophobic membrane covering said vent.

7. The set defined in claim 2, wherein said means associated with said air vent of said first chamber is a hydrophobic membrane covering said vent.

8. The set defined in claim 1 or 2, wherein said means associated with said air vent of said first chamber is a flexible tubing having an air filter at its outer end and a flow control device thereon for controlling the flow of liquid through said tubing.

9. The set defined in claim 2, wherein said means associated with said air vent of said first chamber is a flexible tubing having an air filter at its outer end and a flow control device thereon for controlling the flow of liquid through said tubing.

10. The set defined in claim 1 or 2, wherein said inlet to said second chamber is covered at its outer end by a resealable membrane.

11. The set defined in claim 1 or 2, wherein said air barrier is located between the ends of said secondary tube.

12. The set defined in claim 1 or 2, wherein said primary tube further includes a primary piercing pin at its distal end for insertion into a container for a primary medical liquid and a drip chamber for forming drops of said primary liquid.

13. The set defined in claim 12, wherein said secondary tube further includes a secondary piercing pin at its distal end for insertion into a container for a secondary medical liquid, and a drip chamber for forming drops of said secondary liquid.

14. The set defined in claim 12 or 13, wherein said piercing pins and drip chambers are integral.

15. The set defined in claim 12 or 13, wherein said piercing pins have integral air vents.

16. The set defined in claim 1, wherein said primary flow control means is on the distal side of said primary valve and said primary valve is further characterized as a one-way valve that allows said primary liquid to flow towards said common tube, but prevents the flow of said secondary liquid into said primary tube.

17. The set defined in claim 16, wherein said primary tube further includes a priming tube connected thereto in fluid communication on each side of said primary flow control means and having a priming tube flow control means thereon to regulate the flow of said primary liquid through said priming tube.

18. The set defined in claim 16 or 17 and further including a chamber for a compressible mass in fluid communication with said primary tube between said primary flow control means and said primary valve to provide a spring for relieving pressures on said primary valve whenever the height of said primary liquid is less than the height of said secondary liquid in the system.

19. The set defined in claim 18, wherein said chamber has only one opening thereto.

20. The set defined in claim 18, wherein said chamber has an inlet and outlet in communication with said primary tube.

21. The set defined in claim 18, wherein said compressible mass is air.

* * * * *